(12) United States Patent
Gross et al.

(10) Patent No.: US 6,500,150 B1
(45) Date of Patent: *Dec. 31, 2002

(54) PRE-FILLED DRUG-DELIVERY DEVICE AND METHOD OF MANUFACTURE AND ASSEMBLY OF SAME

(75) Inventors: Joseph Gross, Moshav Mazor (IR); Gilad Lavi, Rishon Letzion (IL); Izrail Tsals, Sudbury, MA (US)

(73) Assignee: Elan Pharma International Limited, Shannon, County Clare (IR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 234 days.

(21) Appl. No.: 09/103,716

(22) Filed: Jun. 23, 1998

Related U.S. Application Data

(60) Provisional application No. 60/093,062, filed on Jun. 24, 1997.

(30) Foreign Application Priority Data

Jun. 16, 1997 (IR) .................................................. 970445

(51) Int. Cl.[7] .......................... A61M 37/00; A61M 5/00; A61M 5/32
(52) U.S. Cl. ....................... 604/131; 604/110; 604/198; 604/263
(58) Field of Search .......................... 604/93, 110, 111, 604/192, 198, 233, 239, 263, 264, 131, 272

(56) References Cited

U.S. PATENT DOCUMENTS

| | | | |
|---|---|---|---|
| 2,605,765 A | * 8/1952 | Kollsman | 128/218 |
| 4,140,117 A | 2/1979 | Buckles et al. | 128/213 R |
| 4,178,928 A | 12/1979 | Tischlinger | 128/215 |
| 4,191,181 A | 3/1980 | Franetzki et al. | 128/213 R |
| 4,196,732 A | 4/1980 | Wardlaw | 128/218 |
| 4,258,713 A | 3/1981 | Wardlaw | 128/218 |
| 4,640,445 A | 2/1987 | Yamada | 222/386.5 |
| 4,684,367 A | 8/1987 | Schaffer | 604/140 |
| 4,687,423 A | 8/1987 | Maget et al. | 417/379 |
| 4,734,092 A | 3/1988 | Millerd | 604/67 |
| 4,753,651 A | 6/1988 | Eckenhoff | 424/449 |
| 4,758,226 A | 7/1988 | Carre | 604/141 |
| 4,772,263 A | 9/1988 | Dorman et al. | 604/132 |
| 4,886,499 A | 12/1989 | Cirelli et al. | 604/131 |
| 4,894,055 A | * 1/1990 | Sudnak | 604/198 |
| 4,902,278 A | 2/1990 | Maget et al. | 604/132 |
| 5,024,656 A | 6/1991 | Gasaway et al. | 604/70 |
| 5,024,661 A | 6/1991 | Wender et al. | 604/110 |
| 5,045,064 A | 9/1991 | Idriss | 604/132 |
| 5,098,385 A | 3/1992 | Walsh | 604/131 |
| 5,135,507 A | 8/1992 | Haber et al. | 604/187 |
| 5,242,406 A | 9/1993 | Gross et al. | 604/132 |
| 5,266,013 A | 11/1993 | Aubert et al. | 417/474 |

(List continued on next page.)

FOREIGN PATENT DOCUMENTS

| | | | |
|---|---|---|---|
| WO | WO 92/11879 | 7/1992 | A61M/1/08 |
| WO | WO 97/10012 | 3/1997 | 5/142 |
| WO | WO 97/21457 | 6/1997 | 5/20 |

*Primary Examiner*—Richard K. Seidel
*Assistant Examiner*—Michael Hayes
(74) *Attorney, Agent, or Firm*—Kathleen M. Lynch

(57) ABSTRACT

A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject.

16 Claims, 21 Drawing Sheets

U.S. PATENT DOCUMENTS

| | | |
|---|---|---|
| 5,312,389 A | 5/1994 | Theeuwes et al. ........ 604/892.1 |
| 5,324,258 A | 6/1994 | Rohrbough .................. 604/86 |
| 5,391,151 A | 2/1995 | Wilmot ....................... 604/139 |
| 5,395,346 A | 3/1995 | Maggioni ................... 604/195 |
| 5,395,501 A | 3/1995 | Rohrbacker et al. ........ 204/265 |
| 5,527,288 A | 6/1996 | Gross et al. ................ 604/140 |
| 5,545,143 A | 8/1996 | Fischell ...................... 604/180 |
| 5,562,624 A | 10/1996 | Righi et al. ................. 604/110 |
| 5,613,951 A | 3/1997 | Meyer et al. ................ 604/110 |
| 5,616,132 A | 4/1997 | Newman .................... 604/185 |
| 5,624,401 A | 4/1997 | Leijd .......................... 604/110 |
| 5,637,092 A | 6/1997 | Shaw ......................... 604/110 |
| 5,785,688 A | 7/1998 | Joshi et al. ................. 604/141 |
| 5,795,336 A * | 8/1998 | Romano et al. ............ 604/192 |
| 5,858,001 A * | 1/1999 | Tsals et al. ................. 604/135 |

* cited by examiner

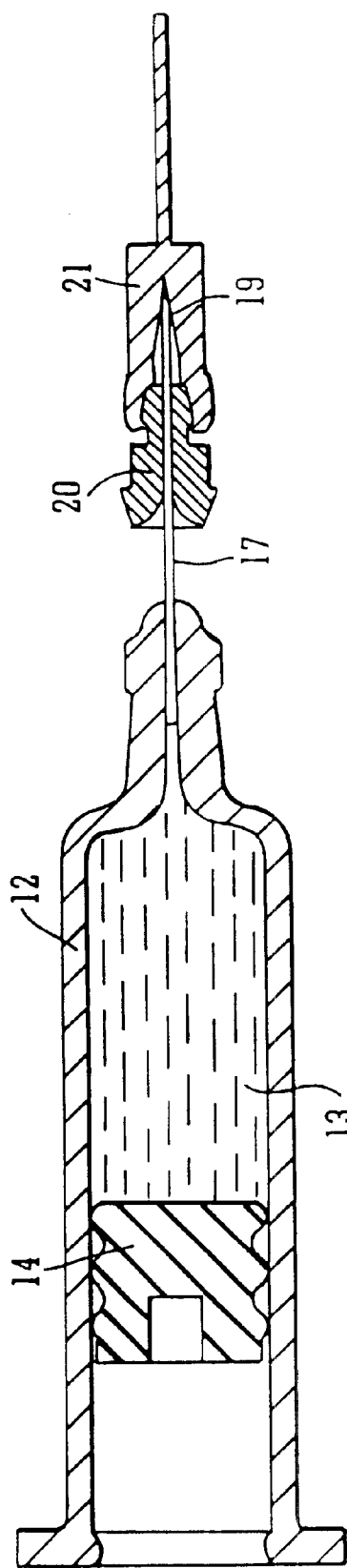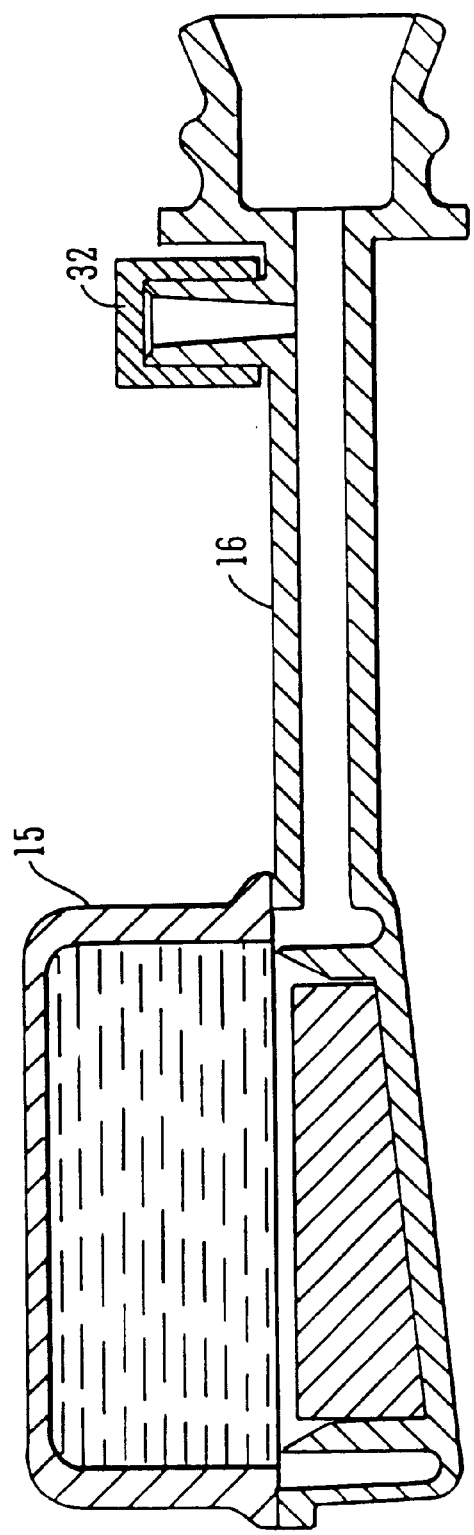
FIG. 14
FIG. 15

PRE-FILLED DRUG-DELIVERY DEVICE AND METHOD OF MANUFACTURE AND ASSEMBLY OF SAME

RELATED APPLICATIONS

This application claims priority under 35 U.S.C. §119(e) of provisional patent application Ser. No. 60/093,062 having a filing date of Jun. 24, 1997 which in turn was converted from a utility patent application Ser. No. 08/881,542 filed on Jun. 24, 1997 which in turn claims priority under 35 U.S.C. §119(a)–(d) of Irish Patent Application No. 970445 filed on Jun. 16, 1997.

TECHNICAL FIELD

This invention relates to pre-filled drug delivery devices, and in particular to devices for attachment to the skin of a subject having a needle for penetration of the skin of the subject.

BACKGROUND OF THE INVENTION

WO 97/21457, which is incorporated herein by reference, discloses a liquid drug delivery device having a base member defining a skin-contacting surface for application to the skin of a subject. A columnar cartridge serving as a reservoir for the drug is connected to the base member such that in use the longitudinal axis of the cartridge is disposed substantially parallel to the skin-contacting surface. A delivery needle communicates in use with the interior of the cartridge and is adapted to penetrate the skin of the subject, and there is provided means for expelling a drug out of the interior of the cartridge and through the skin of the subject via the delivery needle.

It has been found that adapting conventional cartridges (such as cartridges for pen-type insulin injectors, or other drug cartridges well known in the art) so as to enable an expelling means to expel the drug therefrom, and so as to enable communication with a delivery needle forming part of such a device, increases the costs of the cartridge considerably, and this in turn adds to the cost of the overall device and hence its attractiveness to consumers. The main reason for this is that conventional drug cartridges are relatively inexpensive, but redesigning such a component and changing the manufacturing process, or individually modifying such components drives costs up considerably.

Nevertheless, in technical terms, the devices of WO 97/21457 have undoubted advantages over the prior art due to the fact that the disposition of the cartridge parallel to the skin enables the device to be applied to the skin and worn unobtrusively during drug delivery. Both application of the device and delivery of the drug can be accomplished in a single step requiring little or no manual dexterity.

A further problem associated with the devices of WO 97/21457 is in relation to the delivery needle which effectively extends at right angles to the axis of the cartridge. This may be accomplished by using a conduit arrangement leading from the cartridge to a conventional needle, or by means of a right-angled needle which extends from an end of the cartridge co-axially with the axis of the cartridge and then bends through a right angle to penetrate the skin. The latter arrangement is preferred since it reduces the number of parts and the complexity of the device. However, it may prove difficult to bend a needle while maintaining sterility (which is of course essential), since the sterility of the needle is assured by a protective sheath which extends the entire length of the needle and which may be damaged in the bending process.

For devices which employ a needle to penetrate the skin there is a danger that after use the device may accidentally infect the patient or others if not properly disposed of Our WO 95/13838 discloses an intradermal device of this type having a displaceable cover which is moved between a first position in which the needle is retracted before use and a second position in which the needle is exposed during use. Removal of the device from the skin causes the cover to return to the first position in which the needle is again retracted before disposal.

The present invention aims to decrease the possibilities that the needle could become exposed by accident before or after use for example by a child playing with the device if not properly disposed of. Clearly given the risks associated with infectious diseases, particularly those carried by blood, any possibility of accidental infection must be minimised to the utmost and preferably eliminated entirely. Some of the features of devices according to the invention which address these problems are set out below, and further advantages will become apparent from the following description.

In devices of the present invention, a conventional syringe barrel is mounted relative to a base member defining a skin-contacting surface, with the longitudinal axis of the needle substantially parallel to the skin-contacting surface in use.

SUMMARY OF THE INVENTION

The invention provides a base member defining a skin-contacting surface for application to the skin of a subject;

a syringe serving as a reservoir for the drug and which is connected to the base member such that in use the longitudinal axis of the syringe is disposed substantially parallel to the skin-contacting surface;

a delivery needle in communication with the syringe, the needle having an angled bend which directs the tip of the needle substantially perpendicular to the skin-contacting surface such that in use the tip of the needle is adapted to penetrate the skin of the subject; and means for expelling a drug out of the interior of the syringe.

Preferably, the syringe is a pre-filled syringe.

By employing a conventional syringe, preferably a pre-filled syringe, the devices of the present invention avoid the need for custom-designed components for which it may be difficult to obtain regulatory approval and manufacturing validation from bodies such as the U.S. Food and Drug Administration (F.D.A.) and similar other national bodies.

It has been found that while conventional drug-containing components such as cartridges and pre-filled syringes are relatively inexpensive, redesigning such components and changing the manufacturing process, or individually modifying such components drives costs up considerably for the device as a whole, which decreases the attractiveness of such devices to customers. Thus, devices of the present invention which employ widely available syringe bodies will be advantageous over corresponding devices which include a non-standard drug chamber.

Preferably, a mounting member is mounted along the length of the exterior of the needle at the angled portion. Such a mounting member serves two purposes: firstly it acts as a mounting point for a seal or sheath to ensure sterility of the portion of the needle which will contact or penetrate the skin, and secondly it may assist in the correct bending of the needle during the manufacturing process.

Preferably, the mounting member is permanently affixed to the needle.

Further, preferably, a sealing sheath is mounted on the mounting member.

The sheath is preferably removably mounted on the mounting member.

Preferably, means are provided for driving a piston along the interior of the syringe barrel, and these means are also mounted relative to the skin-contacting surface. Preferably, both the syringe barrel and the driving means are mounted within a housing.

In preferred embodiments, the driving means is disposed alongside the syringe barrel rather than at the end thereof, as this arrangement may lead to a more ergonomic design, as well as to advantages in the manner in which the driving means may be actuated as will be explained below in greater detail.

Preferably, the driving means is a gas generator.

Suitably, a tube provides communication between the gas generator and a piston in the syringe.

In one embodiment, the needle extends from the neck of the syringe barrel parallel to the longitudinal axis of the syringe and then bends to a substantially right angle, such that the tip of the needle points perpendicularly to the longitudinal axis of the syringe.

Preferably, the sealing sheath is provided with a flexible pull tab which extends through a release liner.

Further, preferably, when the pull tab is pulled away from the base member, the release liner is pulled away from a lower surface of the base member and the sealing sheath is detached from the mounting member to reveal the needle tip.

In one embodiment, the base member is pivotally mounted to a housing of the device.

Preferably, the device is provided with a removable locking member such as a semi-rigid safety tab which prevents relative movement of the base member towards the housing following removal of the sealing sheath and the release liner, thereby retaining the needle within the housing until skin penetration is required.

Further, preferably, relative motion of the housing towards the base member causes activation of the gas generator while optionally simultaneously causing the needle tip to penetrate the skin.

Preferably, the base member is displaceable relative to the housing between a first position in which the needle is concealed from the exterior of the device and a second position in which the delivery needle protrudes from the device for penetration of the skin, the device further comprising means for locking the device in the first position after a single reciprocation of the device from the first position to the second position and back to the first position.

In this embodiment preferably the locking means comprises a mechanical latch which is brought into operation by said reciprocation.

In an especially preferred embodiment said latch comprises a pair of elements mounted on the base member and the housing respectively, said elements being shaped such that they can have two relative configurations when the base member is in said first position relative to the housing, namely a movable configuration in which the elements are mutually movable, and a locked configuration in which the elements are prevented from mutual movement, and wherein reciprocation of the base member and the housing causes the elements to pass from the first movable configuration, through an intermediate configuration when the base member is in said second position relative to the housing, and then to said locked configuration, thereby preventing any further movement of the base member relative to the housing.

Also preferably one of said elements is provided with a recess which is adapted to receive a projection on the other of said elements, the recess and the projection being spaced apart from one another in the movable configuration, and being in engagement with one another in the locked configuration.

Further, preferably, movement of the base member relative to the housing is initially prevented by said removable locking member.

Still further, preferably, the presence of said removable locking member also prevents the means for providing a gas from being actuated.

The removable locking member preferably comprises a laminar member inserted between said base member and said housing.

In a preferred embodiment following delivery of drug through the needle, any residual gas is vented through a release valve.

In one embodiment means are provided for enabling a user to determine that delivery of drug has been completed.

In a further embodiment, the syringe barrel is provided with an end piston in addition to an internal piston so as to allow for mixing of a drug in a lyophilised form with a diluent, said internal piston initially dividing the interior of the syringe barrel into a diluent compartment and a drug compartment.

Preferably, the pressure resulting from the gas generator is transmitted through the diluent compartment so as to push the internal piston into the drug compartment allowing for ingress of diluent into said drug compartment.

In a further preferred embodiment a travel limiting mechanism is provided to limit the maximum amount of travel of the internal piston along the length of the syringe barrel so that the dose of drug can be adjusted to suit individual user needs.

It will be appreciated that the locking means described herein is capable of having a broad application in drug delivery devices having a drug delivery needle.

Thus in a further embodiment the invention provides a drug delivery device comprising:

a housing having an internal drug reservoir;

a drug delivery needle extending from the housing for penetration of the skin of a subject, the needle having an outlet for drug delivery;

a base member defining a skin-contacting surface for application to the skin of a subject, said base member being displaceable relative to the housing between a first position in which the needle is concealed from the exterior of the device and a second position in which the delivery needle protrudes from the device for penetration of the skin, the device further comprising means for locking the device in the first position after a single reciprocation of the device from the first position to the second position and back to the first position.

Preferably, the base member is pivotally mounted to the housing.

Preferably, the locking means comprises a mechanical latch which is brought into operation by said reciprocation.

Also preferably, said latch comprises a pair of elements mounted on the base member and the housing respectively, said elements being shaped such that they can have two relative configurations when the base member is in said first position relative to the housing, namely a movable configuration in which the elements are mutually movable, and a locked configuration in which the elements are prevented from mutual movement, and wherein reciprocation of the base member and the housing causes the elements to pass from the first movable configuration, through an intermediate configuration when the base member is in said second position relative to the housing, and then to said locked configuration, thereby preventing any further movement of the base member relative to the housing.

Further, preferably, one of said elements is provided with a recess which is adapted to receive a projection on the other of said elements, the recess and the projection being spaced apart from one another in the movable configuration, and being in engagement with one another in the locked configuration.

Still further, preferably, movement of the base member relative to the housing is initially prevented by said removable locking member.

The invention also includes a method of manufacturing and filling drug delivery devices in which a syringe barrel is filled with a drug under sterile conditions, with the fluid path and the skin-contacting and—penetrating portion of the needle also sealed or sheathed under sterile conditions. After this is completed, the remainder of the manufacturing and assembly steps can be carried out in a clean area (as opposed to a sterile area) since the sealed pre-filled syringe barrel remains sterile.

Thus, the invention provides a method for manufacturing and filling a drug delivery device comprising:

providing a base member having a skin-contacting surface; a syringe having drug therein and which is connected to the base member such that in use the longitudinal axis of the syringe is disposed substantially parallel to the skin-contacting surface; a delivery needle in communication with the syringe, the needle having an angled bend which directs the tip of the needle substantially perpendicular to the skin-contacting surface such that in use the tip of the needle is adapted to penetrate the skin of the subject; and means for expelling a drug out of the interior of the syringe, filling the syringe barrel with the drug under sterile conditions with the drug delivery path and the skin-contacting and skin-penetrating portions of the needle under sterile conditions and carrying out the remainder of the manufacturing and assembly steps in a clean area.

The term "clean area" denotes an area of high cleanliness as would be expected for manufacturing medical devices. The term "sterile area" denotes a higher standard of cleanliness (i.e. sterility) such as is required for areas in which syringes are pre-filled. While medical devices must be assembled in clean areas according to well defined standards, the level of cleanliness is not as stringent as for a filling suite in which parenteral drug containers are filled. By pre-filling and sealing all parts of the fluid path, one obtains a component which can be assembled with other components under normal clean area conditions.

Preferably, the sterility of the drug delivery path and the skin-contacting and skin-penetrating portions of the needle is achieved by securely affixing a mounting member along the exterior length of the needle under sterile conditions.

Further, preferably, the drug delivery path and the skin-contacting and skin-penetrating portions of the needle are sealed by means of a sheath mounted on the mounting member.

Preferably, the external mounting member is used as a bending point when a right-angled needle is required.

The sterility of portion of the needle adjacent the needle tip may be assured by securely affixing a mounting member along the exterior length of the needle and ensuring that the mounting member and needle are sterile, following which a sheath or seal is mounted on the mounting member. Subsequent steps of manufacture can then be carried out on the needle without compromising sterility. For example, the external mounting member can be used as a bending point if a right-angled needle is required.

Because of the difficulties in manipulating axially unsymmetric components on a mass-production line, particularly where an unsymmetric part of the component protrudes sideways from an otherwise regular device (e.g. a syringe barrel with a bent needle extending perpendicularly for skin penetration) it is desirable to bend the needle as late as possible in the assembly process.

Conversely, because the sheath guarantees sterility, it is desirable to sheath the needle as early as possible in the manufacturing process (since remaining steps can be carried out in the less expensive clean area).

However, when a seal or sheath is mounted on the neck of the barrel to cover the needle, it is difficult to bend the needle without damaging the sheath and compromising sterility. Equally, it is difficult to mount a sheath on a bent needle since the manipulation may be difficult and the tip of the needle is likely to damage the sheath. Thus, the use of a sterile sheath and the requirement of a bent needle give rise to a conflict as to the most desirable method of manufacture.

The use of a mounting member solves this problem in two respects. Firstly, it enables the sheath to be applied at an early stage (during the filling of the syringe barrel, for example). The sterile barrel can then be removed from the sterile area for further manufacturing/assembly steps. Secondly, the needle can be bent with the sheath intact without having to contact the sheath and risk damage. The needle can be held by the mounting point and bent, and this step can be carried out in a clean environment without any risk to the sterility of the fluid path or the portion of the needle which penetrates or contacts the skin.

In a further aspect the invention provides a method of delivering drug to a subject comprising the steps of:

providing a drug delivery device having a skin-contacting surface, a syringe having drug therein, and which is connected to the base member such that in use the longitudinal axis of the syringe is disposed substantially parallel to the skin contacting surface, a delivery needle in communication with the syringe, the needle having an angled bend, and means for expelling a drug out of the interior of the syringe;

applying the device to the skin of the subject; and activating the device.

Preferably, the tip of the delivery needle is substantially perpendicular to the skin contacting surface such that in use the tip of the needle is adapted to penetrate the skin of the subject.

Also preferably, the the means for expelling the drug comprises a gas generator.

Further, preferably, the syringe is prefilled.

Also preferably the device is activated by moving the housing towards the base member.

Preferably, the movement of the housing simultaneously causes the needle to penetrate the skin.

Further, preferably, the method comprises the step of causing the device to lock into position after use whereby the needle tip is recessed within the housing.

Other objects, features and advantages of the present invention will become apparent upon reading the following detailed description of the embodiments of the invention, when taken in conjunction with the drawings and appended claims.

BRIEF DESCRIPTION OF THE DRAWINGS

The invention will be further illustrated by the following description of embodiments thereof, given by way of example only with reference to the accompanying drawings.

FIGS. 14–18 are sectional side views components of the device of FIG. 1, shown during successive stages of manufacture;

DETAILED DESCRIPTION OF THE INVENTION

Figure 1:
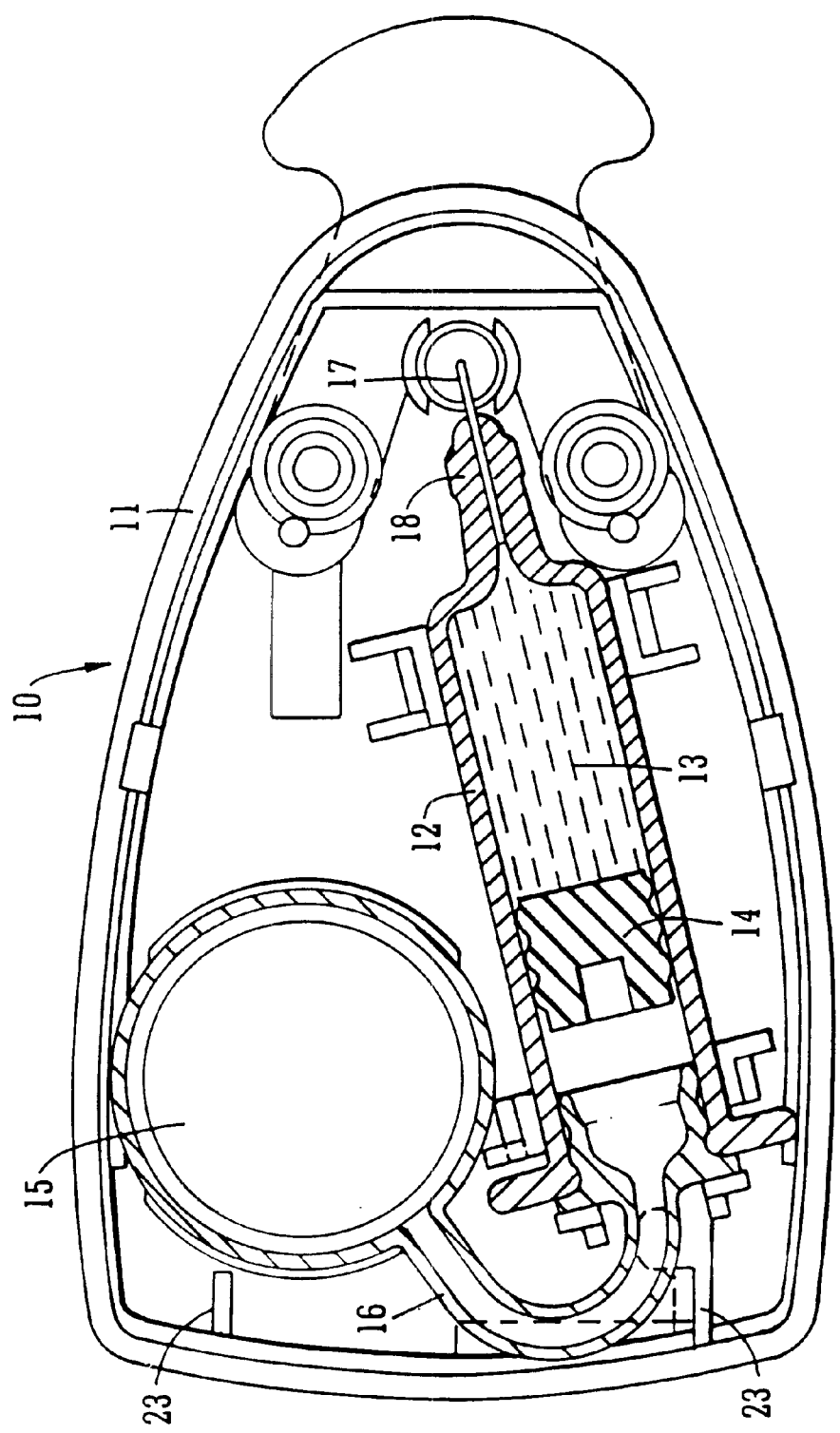
FIG. 1 is a sectional plan view of a drug delivery device according to the invention.

In FIG. 1 there is indicated, generally at 10, a drug delivery device according to the invention. The device 10 comprises a housing 11 in which a standard hypodermic syringe barrel 12 is mounted. A drug 13 is contained in the syringe barrel 12 and the drug is sealed by a conventional syringe piston 14.

A gas generator 15 which will be described in greater detail below is mounted in the housing alongside syringe barrel 12, and a tube 16 provides communication between gas generator 15 and piston 14.

A needle 17 is mounted in conventional manner at the neck 18 of syringe barrel 12 to provide a conduit for delivery of drug 13 from syringe barrel 12 under an applied pressure from piston 14.

Figure 2:
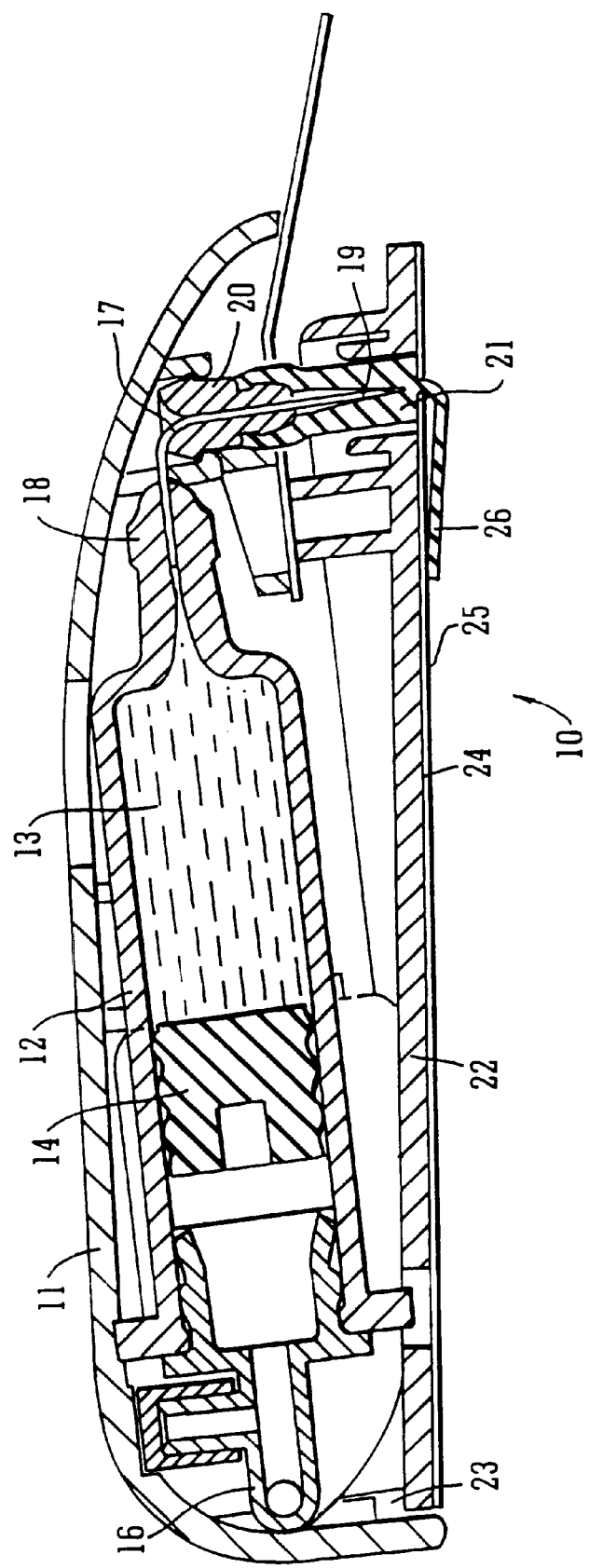
FIG. 2 is a sectional side view of the device of FIG. 1, shown after assembly.

Referring to FIG. 2, the device 10 can be seen in sectional elevation with housing 11, syringe barrel 12, drug 13, piston 14, tube 16 and needle 17 visible. It will be seen that needle 17 extends from neck 18 of syringe barrel 12 parallel to the longitudinal axis of syringe barrel 12, and that needle 17 then bends through a right angle such that the tip 19 points perpendicularly to the longitudinal axis of syringe barrel 12. A plastics mounting member 20 is permanently affixed to needle 17, and a protective sealing sheath 21 is removably mounted on mounting member 20. Protective sealing sheath maintains the sterility of needle 17 below mounting member 20, and in particular needle tip 19.

Housing 11 has a base member 22 pivotally mounted thereon at a hinge 23. The lower surface 24 of base member 22 is provided with a contact adhesive layer (not shown) and a release liner 25 covers the lower surface 24 before use.

Figure 3:
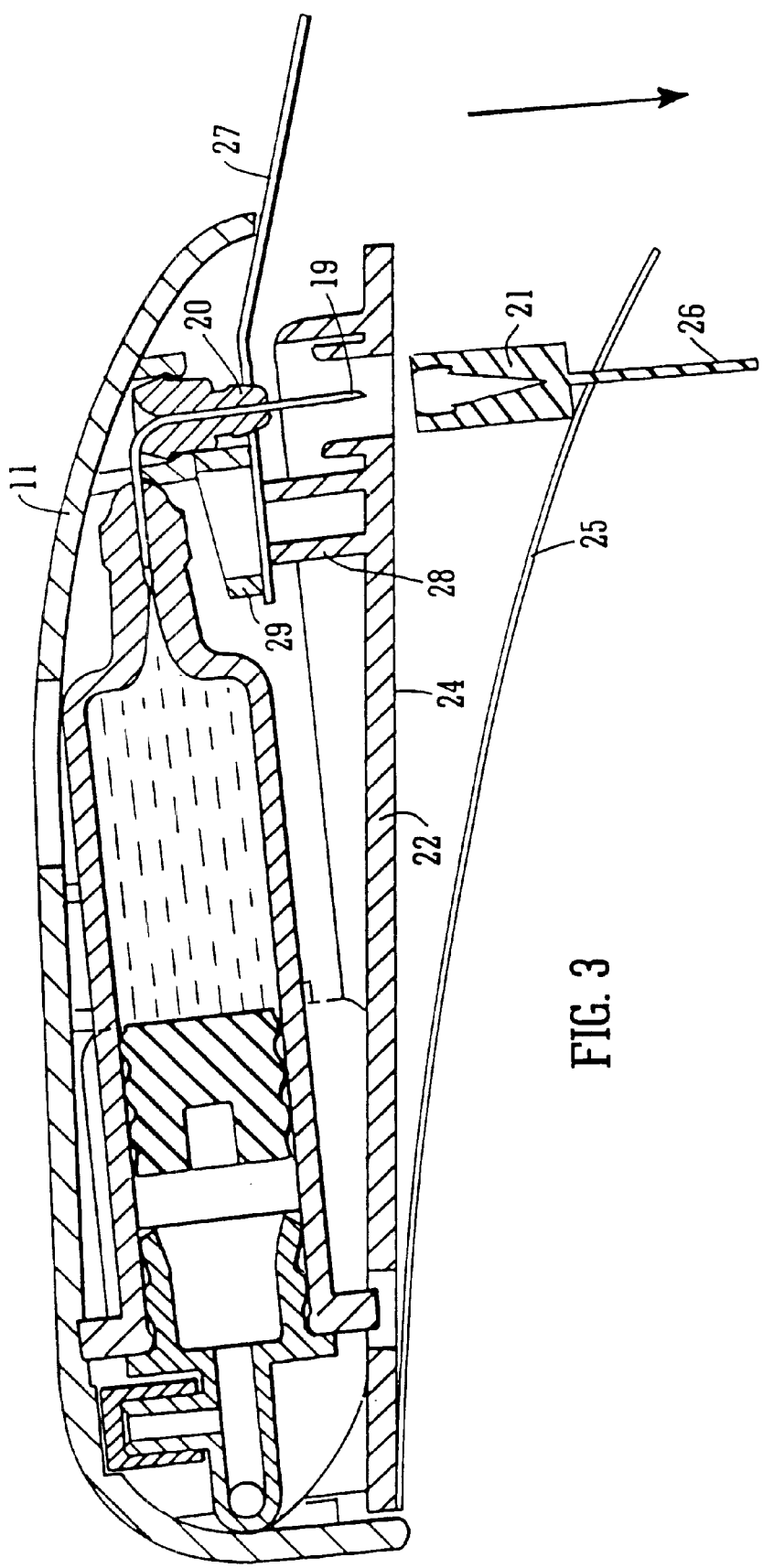
FIGS. 3–5 are sectional side views of the device of FIG. 1, shown in successive stages of preparation and deployment for application to the skin of a subject.

Protective sealing sheath 21 is provided with a flexible plastics pull tab 26 which extends through release liner 25. When pull tab 26 is pulled away from base member 22 (FIG. 3), release liner 25 is peeled away from lower surface 24 and sealing sheath 21 is detached from mounting member 20 to reveal needle tip 19. Needle tip 19 is still somewhat concealed from full exposure by base member 22 which is hinged away from housing 11.

Following the removal of sealing sheath 21 and release liner 25, the lower surface 24 is applied to the skin to which it adheres. A semi-rigid safety tab 27 prevents relative movement of base member 22 towards housing 11 by passing above a first cylindrical post 28 integral with base member 22 and below a second cylindrical post 29 integral with housing 11. Although first cylindrical post 28 is adapted to fit inside second cylindrical post 29 and thereby allow base member 22 to move towards housing 11 about hinge 23, safety tab 27 prevents this when present.

FIG., 4 shows device 10 when safety tab 27 has been removed. A snap action mechanism (not shown) holds the device 10 in the configuration shown in FIG. 4, but downward pressure on the upper surface 30 of housing 11 causes the housing 11 to snap towards base member 22 (mounted on the subject's skin) as shown in FIG. 5. This causes needle tip 19 to shoot through an aperture 31 in base member 22 and thus through the subject's skin (not shown).

As will be further explained below, the relative motion of housing 11 towards base member 22 also causes the activation of gas generator 15 (not visible in FIGS. 2–5), and thus at the same moment that needle tip 19 penetrates the subject's skin, the gas generator 15 begins to generate gas, thereby increasing the pressure in tube 16 which in turn causes a driving force to be exerted on piston 14 to drive drug 13 through needle 17 for delivery to the subject. Such delivery is preferably subcutaneous, although it could also be intravenous, intramuscular or intradermal (i.e. to a point within the dermis below the epidermis), depending on the configuration of the needle and the positioning of the device on the skin of the subject.

Figure 6:
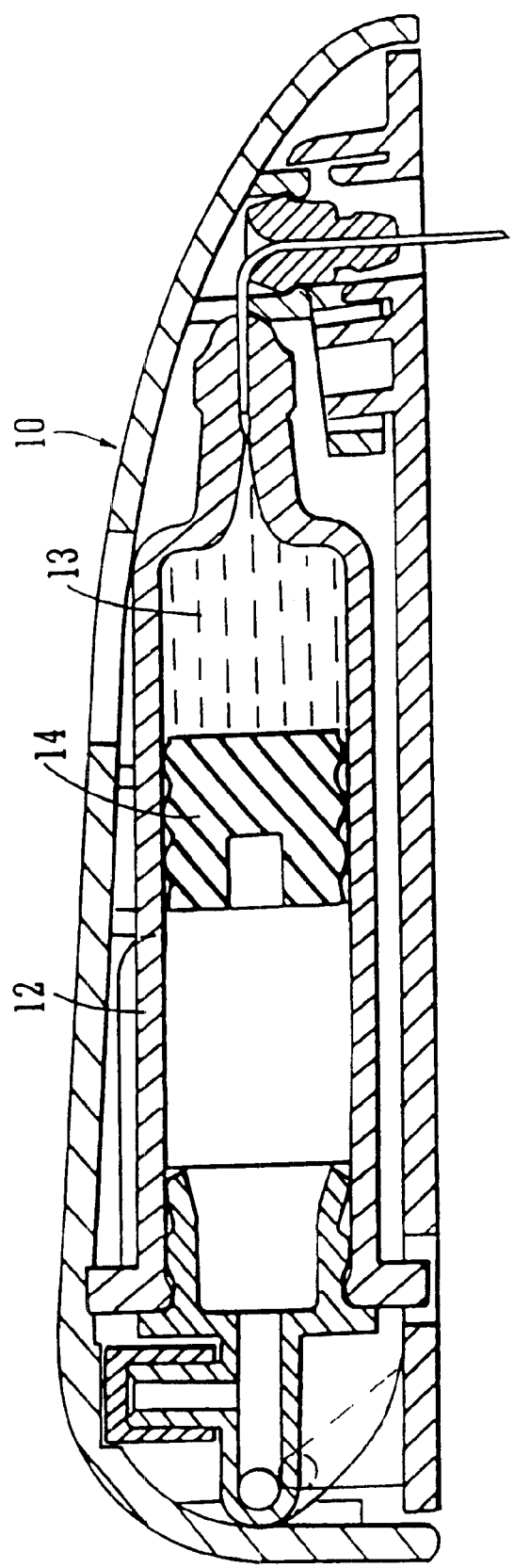
FIGS. 6 and 7 are sectional side views of the device of FIG. 1, shown during and at the end of delivery, respectively.
Figure 7:
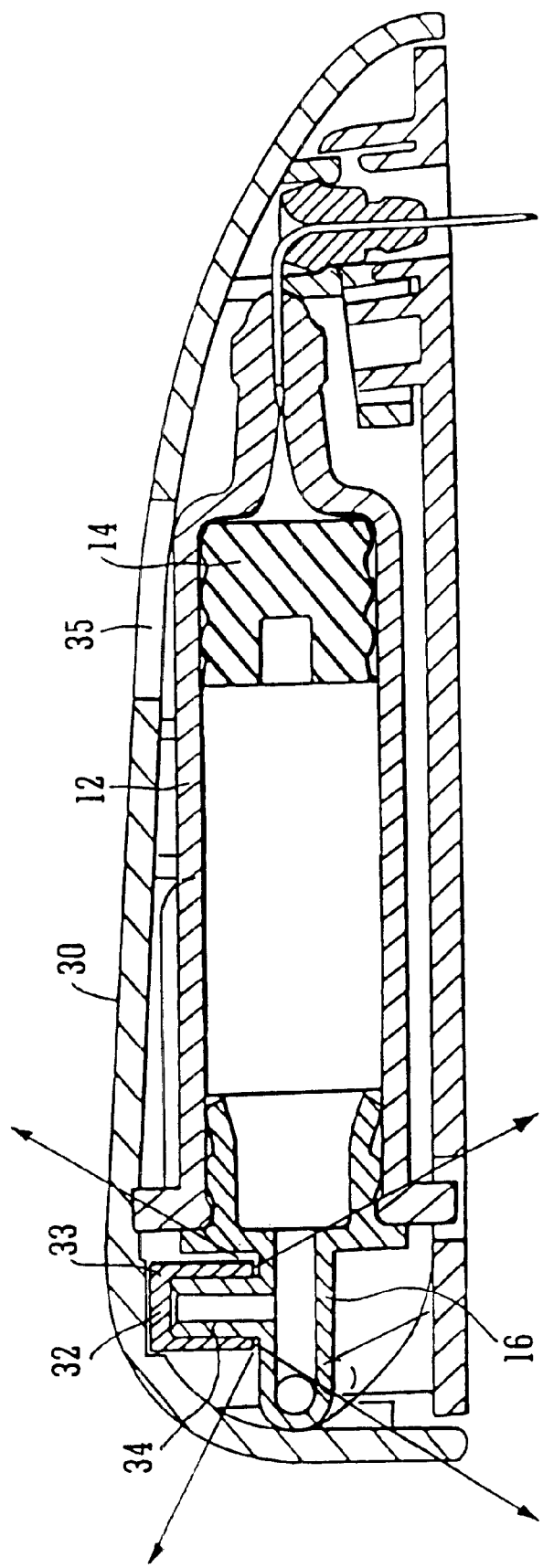

FIGS. 6 and 7 show the device during delivery of the drug and when delivery has been completed, respectively. Thus, in FIG. 6, piston 14 has moved approximately half-way along the length of syringe barrel 12 (and delivered a corresponding fraction of the drug 13 to the subject).

In FIG. 7, the piston 14 has reached the end of syringe barrel 12 and can travel no further. At this point, the gas generator will still be generating a residual amount of gas, and a release valve 32 is provided to enable the escape of excess gas into the housing (and thus to the atmosphere) as indicated by the arrows in FIG. 7. Release valve 32 is a simple mechanism comprising a cap 33 which seals a vent 34 under normal operating conditions and which allows gas to escape in the event of a predetermined overpressure within tube 16.

Figure 8:
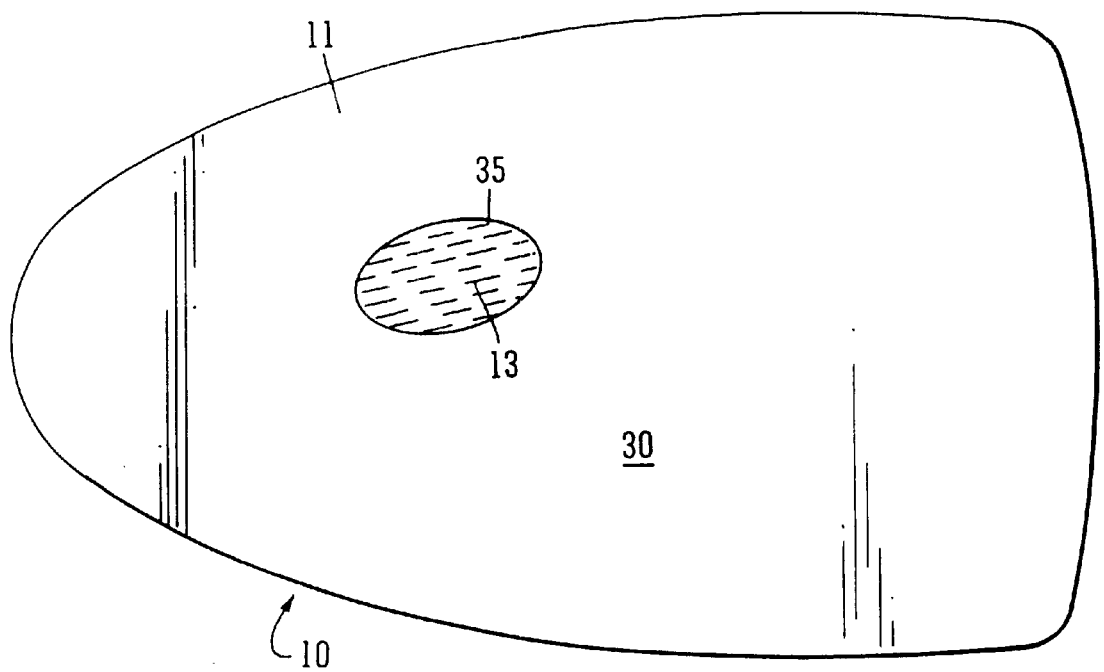
FIGS. 8 and 9 are plan views of the device of FIG. 1, shown during and at the end of delivery, respectively.
Figure 9:
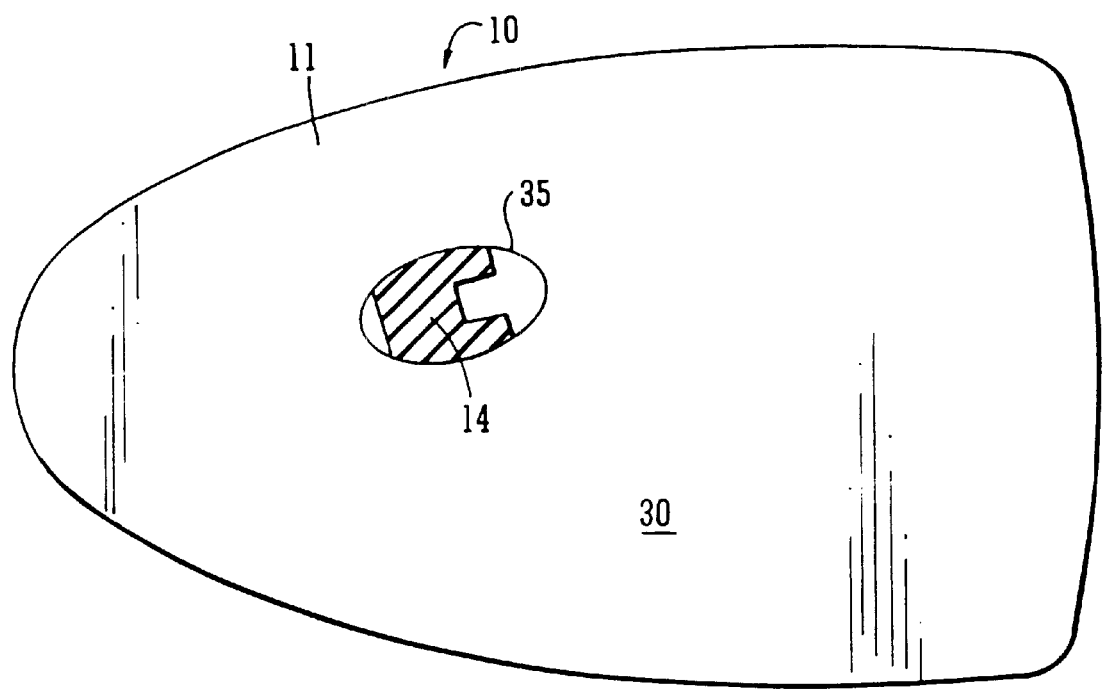

Syringe barrel 12 is formed of a transparent material and a window 35 in upper surface 30 of housing 11 enables the user to see that delivery has been completed. FIGS. 8 and 9 show the upper surface 30 of housing 11 before delivery and when delivery is finished, respectively. Thus in FIG. 8, the user can see drug 13 and in FIG. 9, the user can see that the piston 14 has reached the end of its travel and thus that device 10 should be removed.

Figure 10:
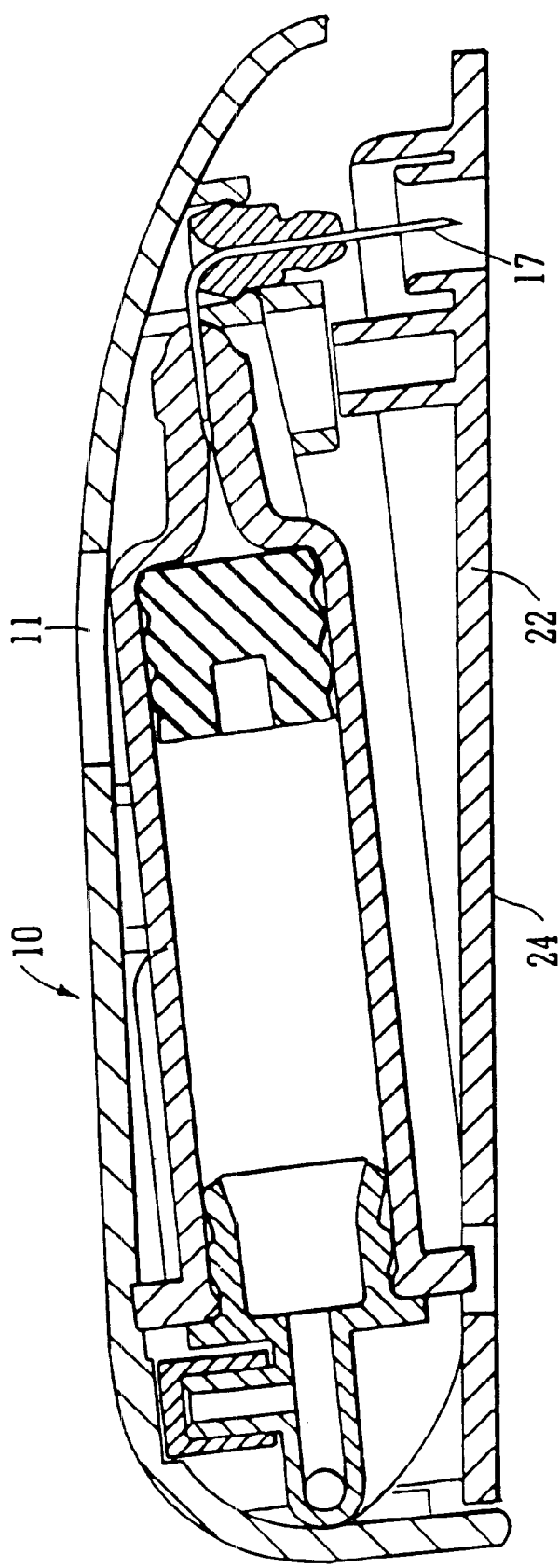
FIG. 10 is a sectional side view of the device of FIG. 1, shown after the device has been removed from the skin.

FIG. 10 shows the device 10 when it is removed. To remove the device 10 the user pulls housing 11 away from the skin. Before the adhesive force between the lower surface 24 and the subject's skin is overcome, the snap mechanism (which is designed to provide a lesser resistance to the tractive force exerted in pulling the housing from the skin) snaps to cause housing 11 to move away from base member 22, such that when lower surface 24 is peeled from the skin the needle 17 is already recessed as shown in FIG. 10. This helps avoid accidental injury or infection and makes the device safer to handle and to dispose of.

The operation of the gas generator 15 will now be described with reference to FIGS. 11–13, each of which is a sectional elevation taken on a line through the device 10 which passes through the centre of the gas generator 15 rather than along the axis of the syringe barrel 12. Thus, with reference to FIG. 1, the elevations of FIGS. 2–7 and 10 are taken along the longitudinal axis of the syringe barrel 12, whereas the elevations of FIGS. 11–13 are taken along a line which is parallel to the longitudinal axis of the device itself, passing through the centre of gas generator 15.

Figure 4:
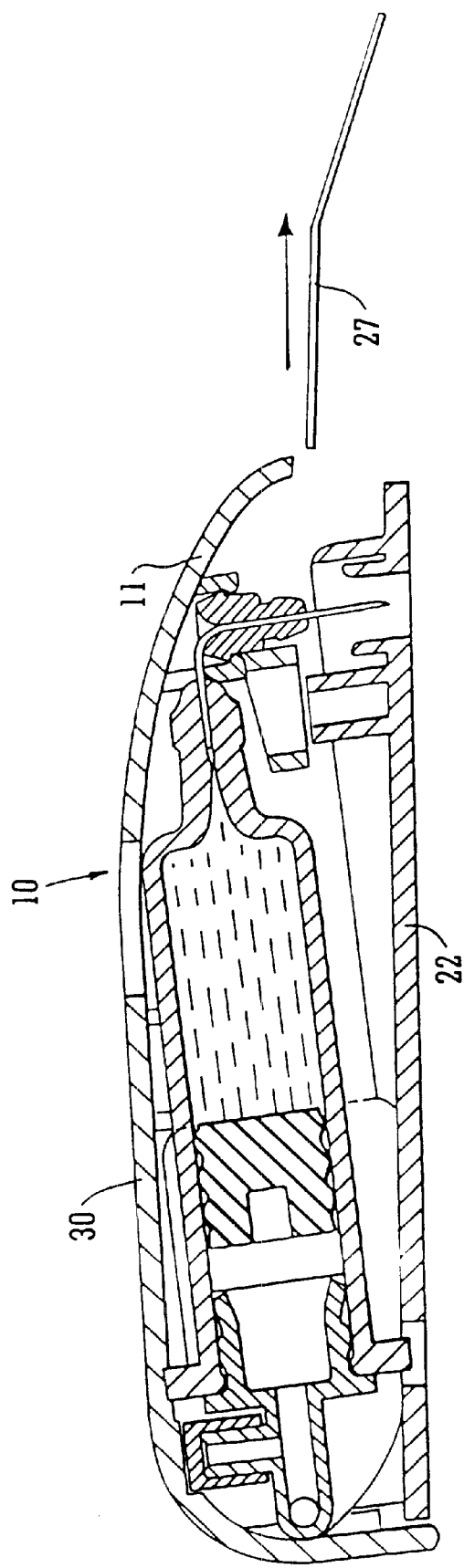
Figure 5:
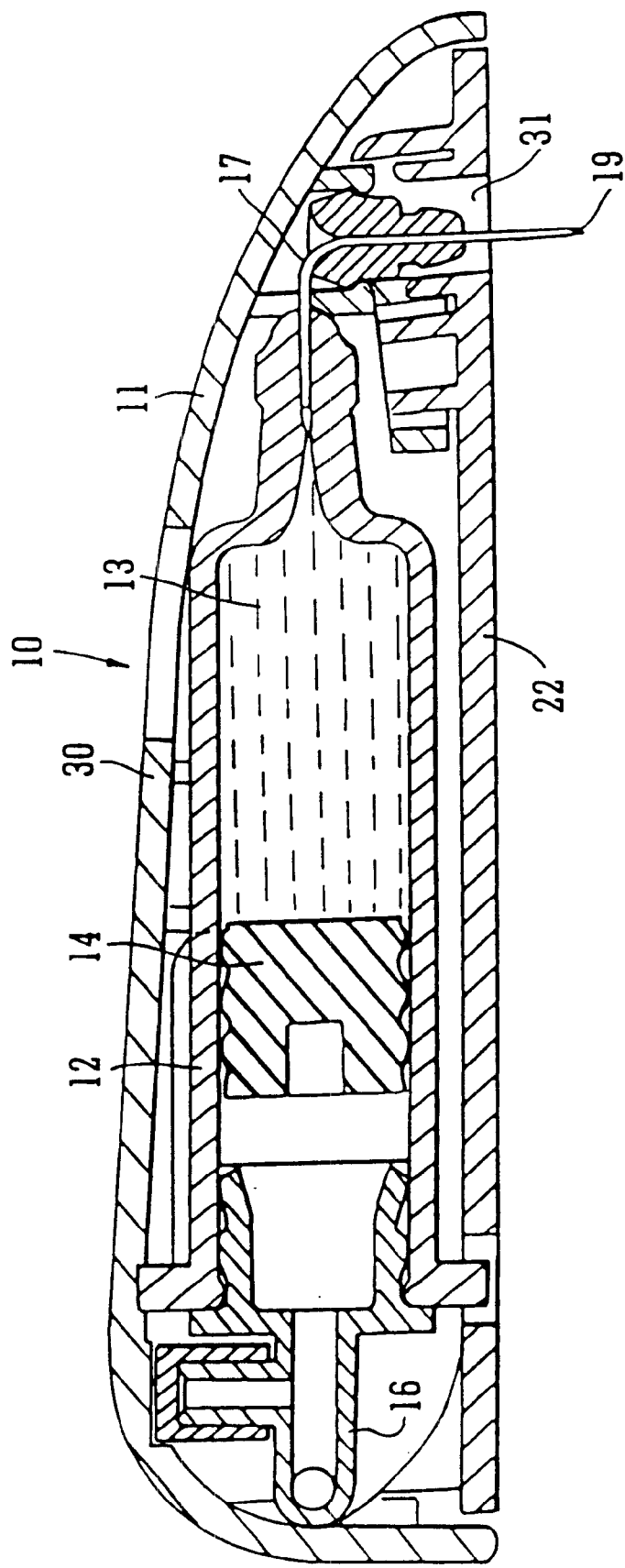
Figure 11:
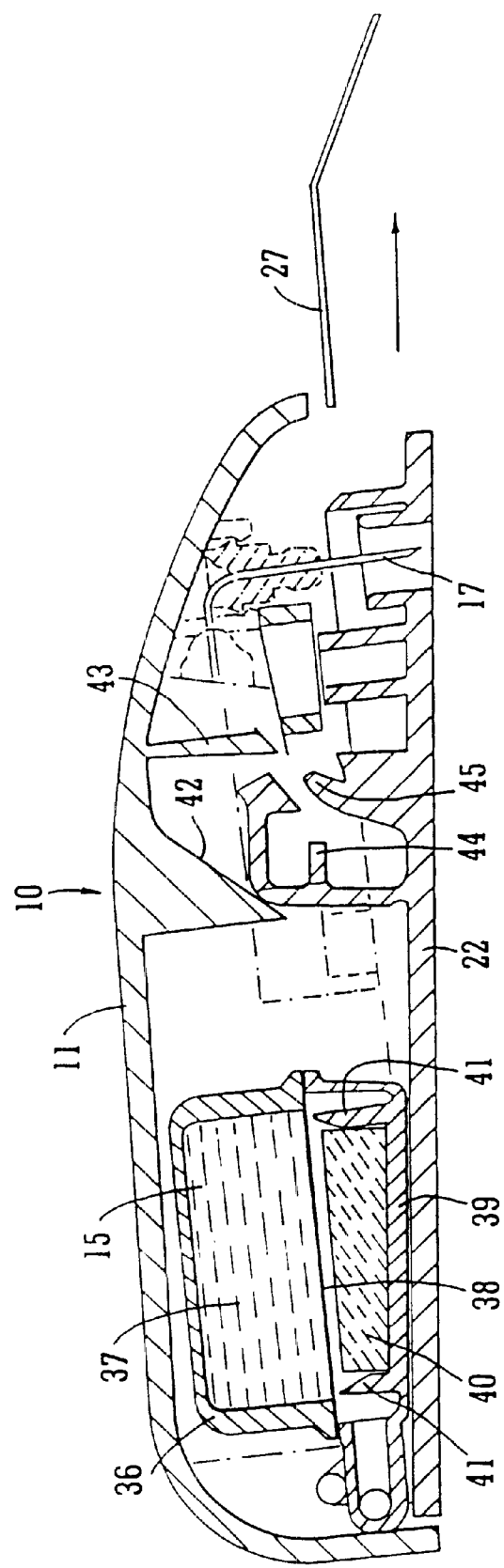
FIGS. 11–13 are sectional side views of the device of FIG. 1 taken through the gas generator, at successive stages corresponding to FIGS. 4,5 and 10, respectively.

FIG. 11 shows device 10 upon removal of the safety tab 27 but before the housing 11 is snapped towards base member 22 (i.e. at the same moment as is shown in FIG. 4). Gas generator 15 comprises an upper chamber 36 filled with citric acid solution 37 and sealed on its underside by a foil membrane 38 before use, and a lower chamber 39 containing a quantity of sodium bicarbonate 40 and means 41 for penetrating the foil membrane 38 when upper chamber 36 is pushed towards lower chamber 39.

Figure 12:
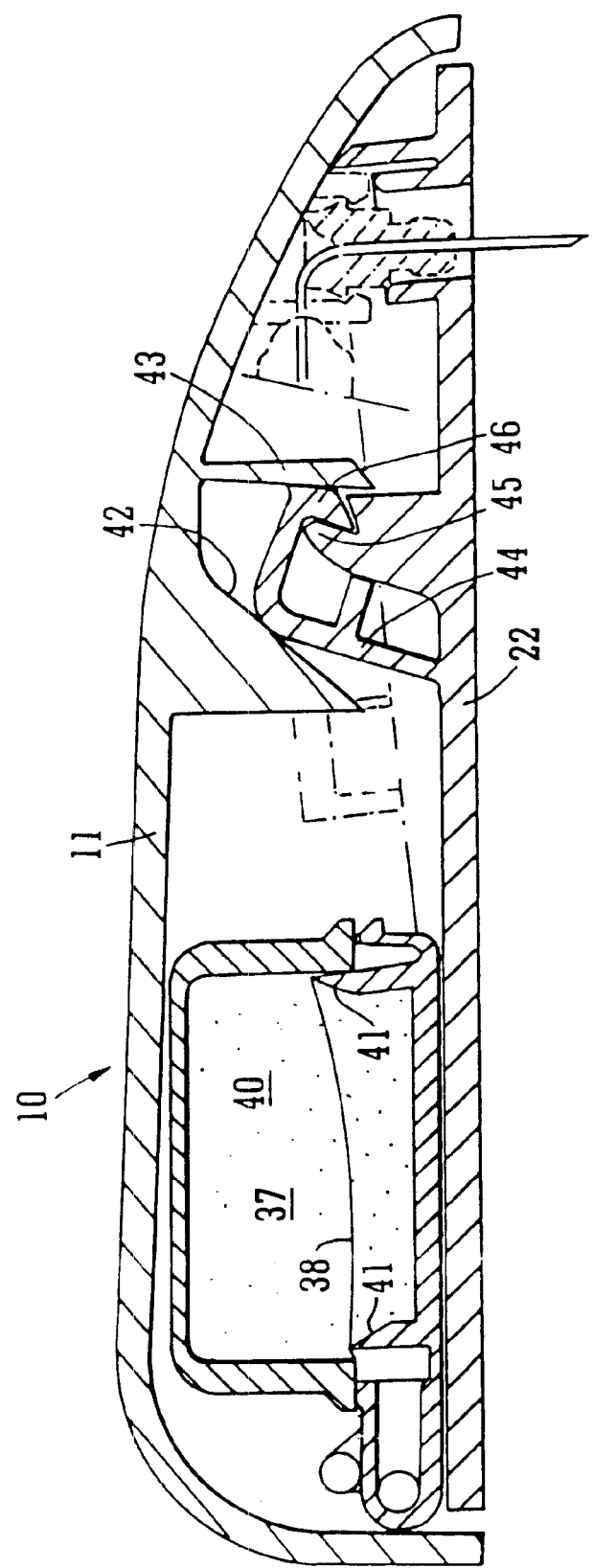
Figure 13:
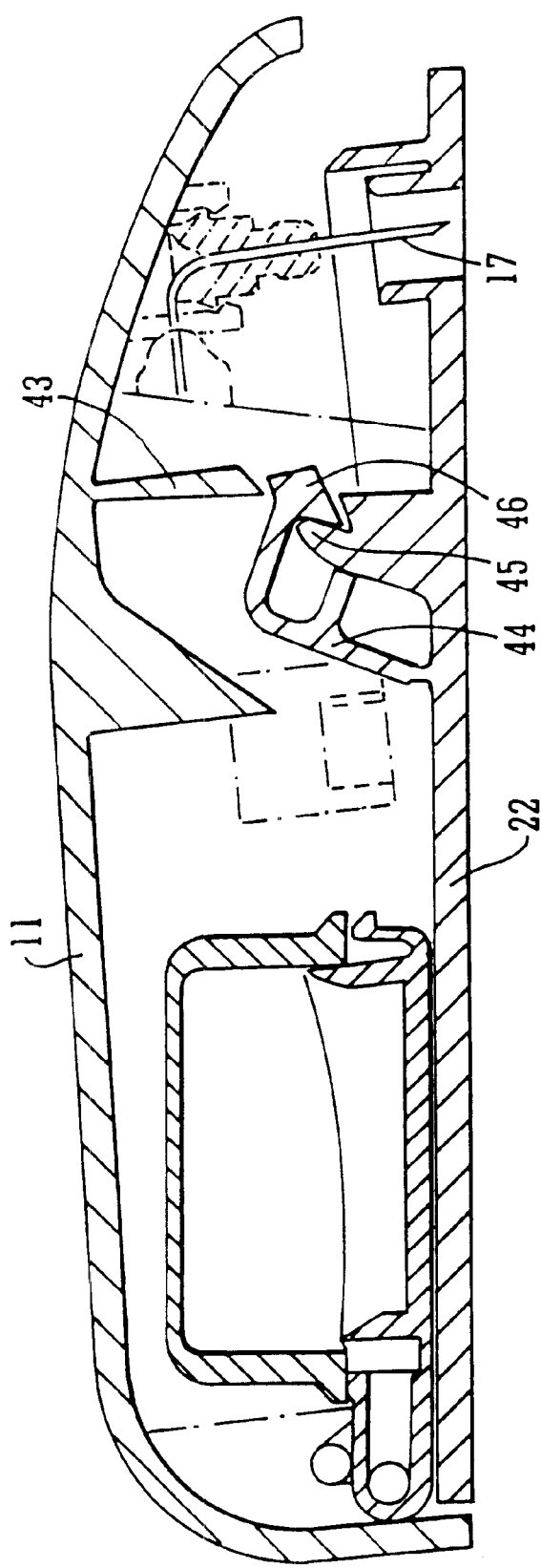

As shown in FIG. 12, when the housing 11 of device 10 is snapped towards base member 22 (i.e. at the moment illustrated in FIG. 5), the foil membrane 38 is penetrated by penetrating means 41. This causes the citric acid 37 to mix with the sodium bicarbonate 40 to thereby generate gas and drive piston 14 (not shown in FIGS. 11–13) as previously described.

Because the gas generator 15 is situated alongside syringe barrel 12 rather than at the end thereof, it is further from the hinge 23 than would otherwise be the case. It may be preferred to move the gas generator 15 further from the hinge 23 than is shown in the present embodiment (see FIG. 1). This would mean that the action of pushing housing 11 towards base member 22 (i.e. pivoting housing 11 and base member 22 together about hinge 23) is more effective in causing the penetration of foil membrane 38, since the further the distance a body is from the fulcrum of a lever, the greater the linear movement is for a given angular movement about the fulcrum. For this reason also, the needle 17 can penetrate the skin with a quick painless action because the needle travels in a predominantly vertical fashion which minimises penetration and thus any pain involved therein. If the needle were closer to the hinge, it would travel in a more circular pattern creating a larger pathway upon penetration and consequently cause more pain. A further advantage of moving gas generator 15 away from hinge 23 results from the fact that the citric acid 37 and sodium bicarbonate 40 are mixed to a greater extent (again due to the higher speed at which the foil membrane 38 is penetrated), and gas generation is thereby smoother.

FIG. 13 shows the device when the housing 11 has been retracted from the base member 22 and gas generation is completed (equivalent to the view in FIG. 10).

FIGS. 11–13 also illustrate a tamper-proof safety mechanism which ensures that device 10 is a single use device and that the needle 17 cannot be re-deployed after removal from the skin of a subject.

Thus, in FIG. 11 there is shown a sloped surface 42 integral with housing 11 and a post 43 connected to housing 11 in a resiliently flexible manner. A generally "F"-shaped member 44 is connected to base member 22 in a resiliently flexible manner, and a catch 45 adapted to receive and retain "F"-shaped member 44 is integral with base member 22.

As shown in FIG. 12, when housing 11 is pushed towards base member 22, sloped surface 42 engages "F"-shaped member 44 and pushes a projection 46 over catch 45. Projection 46 deflects post 43 at the same time. When housing 11 is pulled away from base member 22 at the end of delivery (FIG. 13), post 43 clears the top of projection 46 (which is held in the FIG. 12 position by catch 45), and post 43 returns to the relaxed position as in FIG. 11. At this stage, the device is locked and no further movement of housing 11 relative to base member 22 is possible because projection 46 prevents any downward movement of post 43. Thus, the needle 17 can only be deployed on a single occasion, i.e. when the device is applied to the skin for the first time.

As previously indicated, the invention provides a method of manufacture which utilises a standard hypodermic syringe and which allows a sterile sheathed needle to be bent without risk of compromising the sterility. A method of manufacturing the device of FIGS. 1–13 will now be described to illustrate these advantages.

In FIG. 14 the syringe barrel 12 is shown prior to assembly in the device according to the invention. Thus, there is shown a standard hypodermic syringe barrel 12 with a standard piston 14 sealing a drug 13, and with a needle 17 mounted thereon in conventional manner. The syringe barrel is filled with the drug and sealed with the piston in the manner currently used for filling pre-filled syringes. After attaching the needle 17 to the syringe barrel 12, the mounting member 20 is permanently attached to the needle and this assembly is sterilised (such as by steam sterilisation or gamma irradiation), and a protective sterile sealing sheath 21 is mounted on the mounting member 20.

The assembly shown in FIG. 14 can be safely removed to a clean room for all further manufacturing/assembly steps in the knowledge that the internal fluid path (i.e. the sealed interior of syringe barrel 12) and the internal bore of needle 17) is sterile, as is the portion of the needle from the tip 19 to the mounting member 20. It is important to note that the needle 17 as shown in FIG. 14 is axially symmetric, i.e. it can be moved around a production line without difficulty (the same would not necessarily be true if the needle were already bent).

FIG. 15 shows the gas generator 15 and tube 16 (including valve 32) during manufacture. Tube 16 is straight initially which again assists in handling in a mass production environment.

Figure 16:
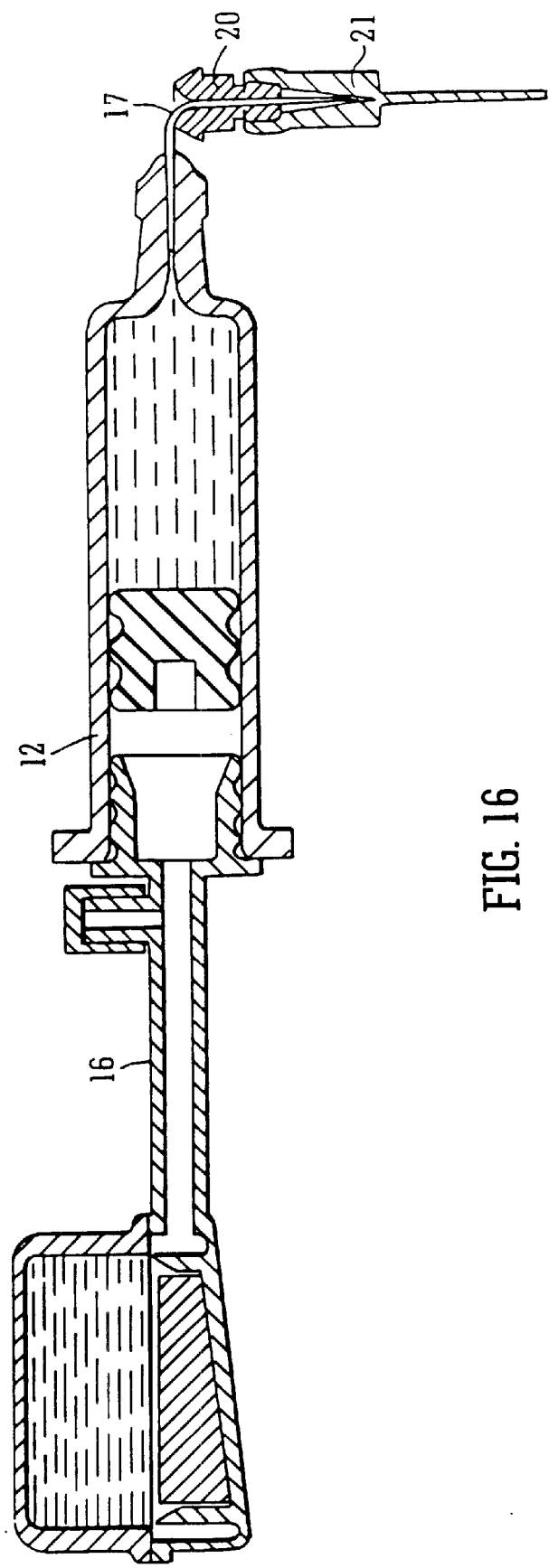

Outside the sterile area, i.e. in a clean room, the tube 16 is mounted on the syringe barrel 12 (see FIG. 16) and the needle 17 is bent by manipulating the mounting member 20, i.e. without manipulating sheath 21. Mounting member 20 is shaped to ensure a smooth bend.

Figure 17:
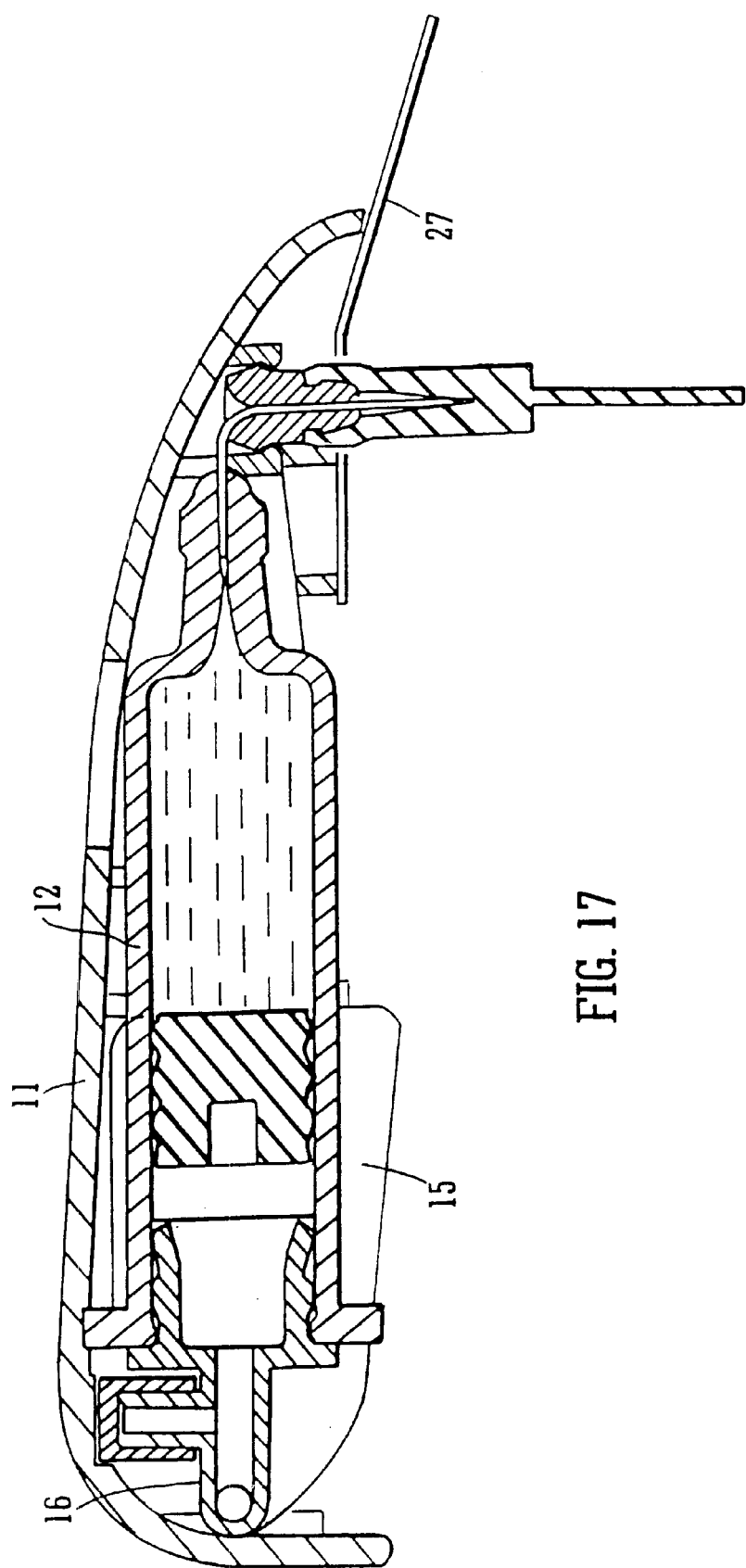

Referring next to FIG. 17, the assembly of gas generator 15, tube 16 and syringe barrel 12 is mounted in housing 11 and safety tab 27 is fitted in position. Tube 16 may be completely flexible or it may be permanently bent into the required curved shape before being fitted to housing 11.

Figure 18:
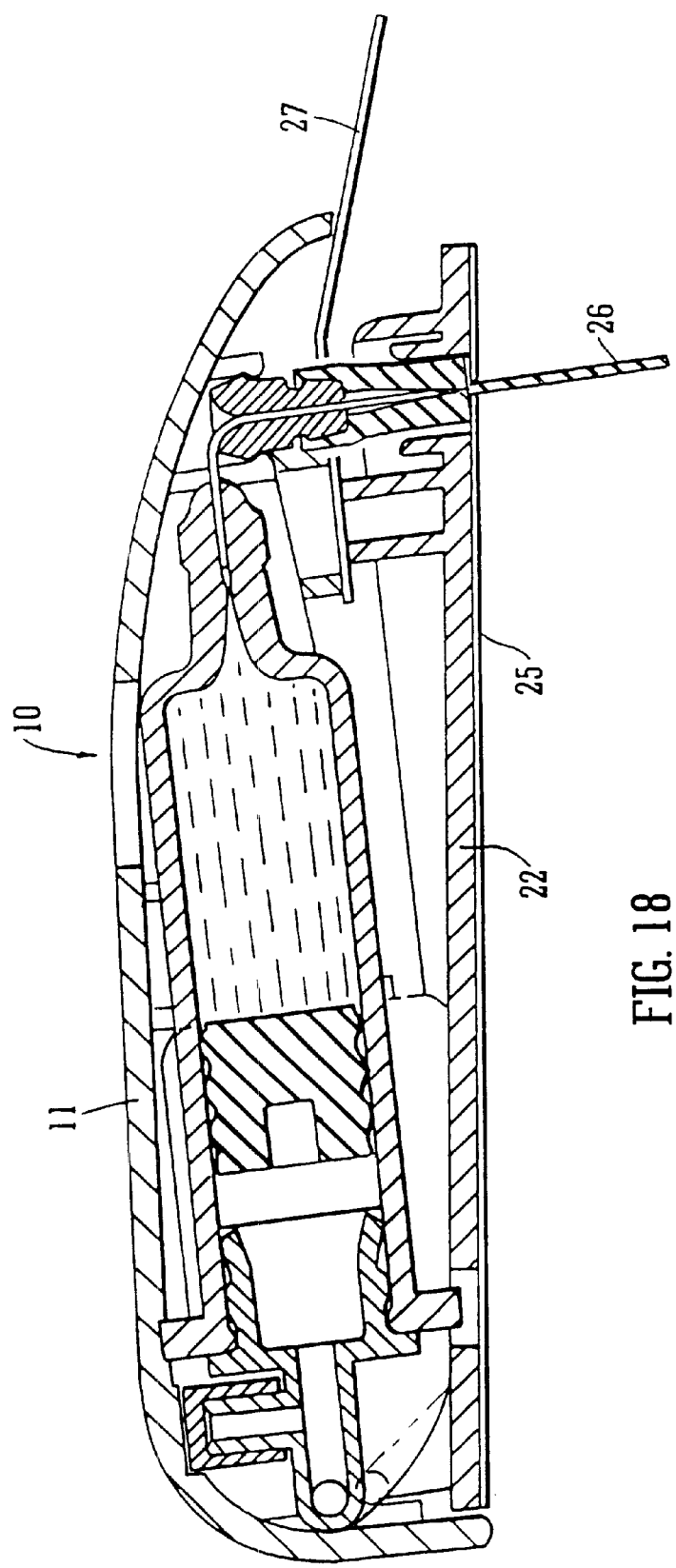

FIG. 18 shows the device when base member 22 is connected to housing 11. Base member 22 is fitted with release liner 25 already in position, so that it is only necessary to fit pull tab 26 through an aperture provided in release liner 25 for this purpose. Device 10 is then ready to be packaged, although it may be desired to fold pull tab 26 to lie against release liner 25 (as illustrated in FIG. 2).

It can be seen that the design of the device allows the majority of the manufacture and assembly to occur outside a sterile area while still ensuring that those parts of the device for which sterility is required remain sterile.

Figure 19:
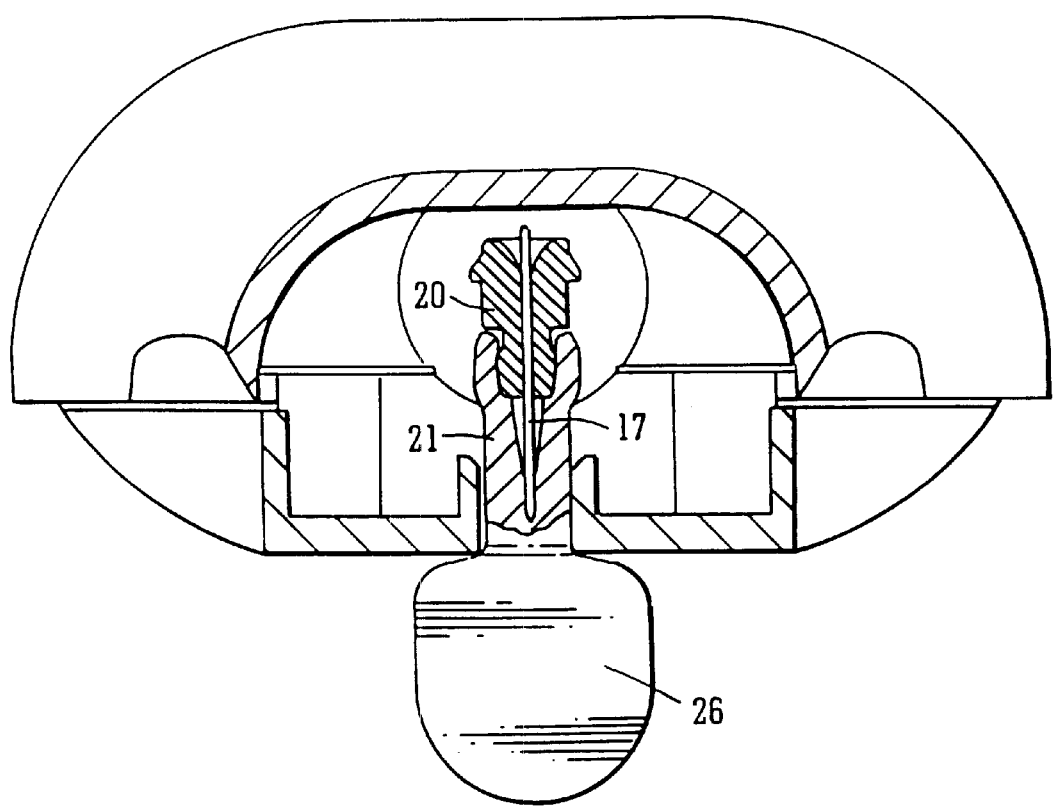
FIG. 19 is a cross-sectional side view of the device of FIG. 1, taken through the needle thereof.

FIG. 19 shows a sectional view through needle 17, mounting member 20, protective sealing sheath 21 and pull tab 26 which illustrates the exact assembly of these components.

Figure 20:
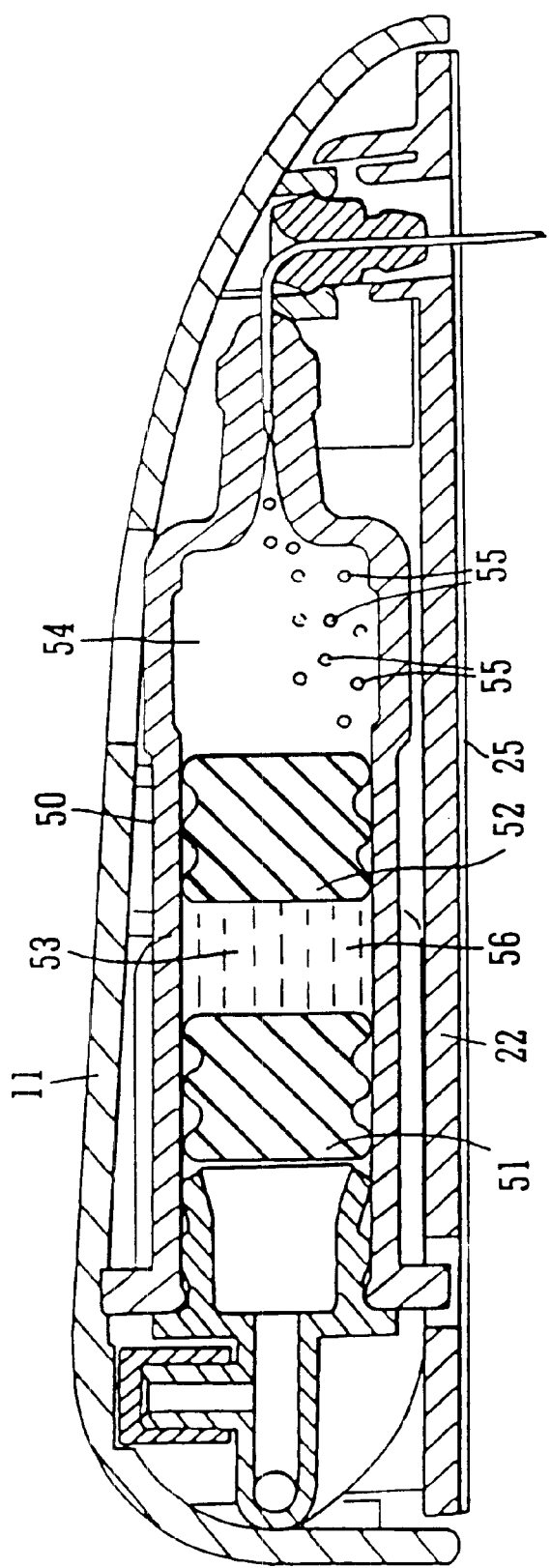
FIGS. 20–22 are sectional side views of an alternative embodiment of a device according to the invention, which enables a lyophilised drug to be reconstituted and delivered to a subject.

FIG. 20 shows a variant on the device already illustrated, in which like numerals are designated by like reference numerals, the only difference being that the syringe barrel 12 is of the type used for drugs which are provided in lyophilised form and mixed with diluent prior to use. Such syringe barrels are known in the art.

The barrel 50 is provided with an end piston 51 which is acted on by gas pressure from a gas generator as previously described. An internal piston 52 initially divides the interior of syringe barrel 50 into a diluent compartment 53 and a drug compartment 54. The internal bore of the syringe barrel 50 is greater in the drug compartment 54 than in the diluent compartment 53. Thus, while internal piston 52 makes a sealed sliding fit with the narrower bore, it becomes loose in the wider bore of the drug compartment. Alternatively, the barrel could be of a constant diameter with a channel along part of the interior surface providing a pathway for the diluent. A lyophilised drug 55 is provided in the drug compartment together with a quantity of entrapped air. Diluent compartment 53 is entirely filled with liquid diluent 56 suitable to reconstitute the drug 55.

Figure 21:
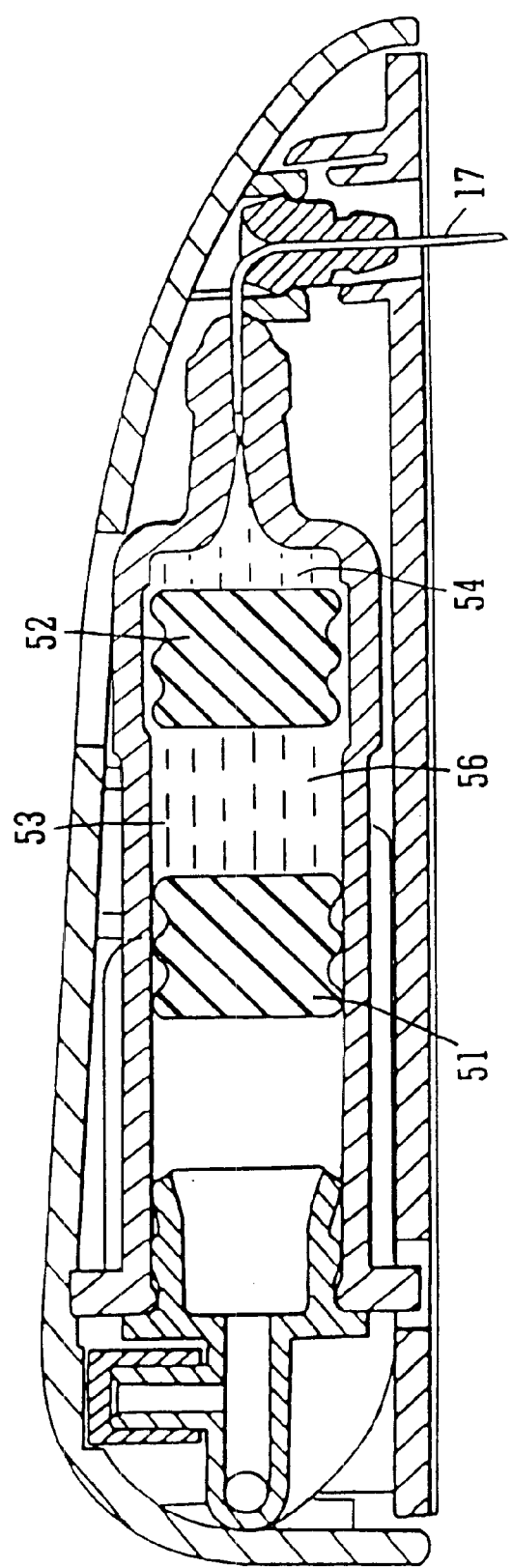

When gas generation begins, the pressure acting on end piston 51 is transmitted through the diluent 56 to push internal piston 52 towards drug compartment 54. Continued gas generation pushes internal piston 52 entirely into drug compartment 54 (FIG. 21) and allows the ingress of diluent 56 into drug compartment 54 where the diluent reconstitutes the drug into solution. Continued pressure on end piston 51 forces the reconstituted drug solution out through the needle 17 to the subject for delivery as previously described.

Figure 22:
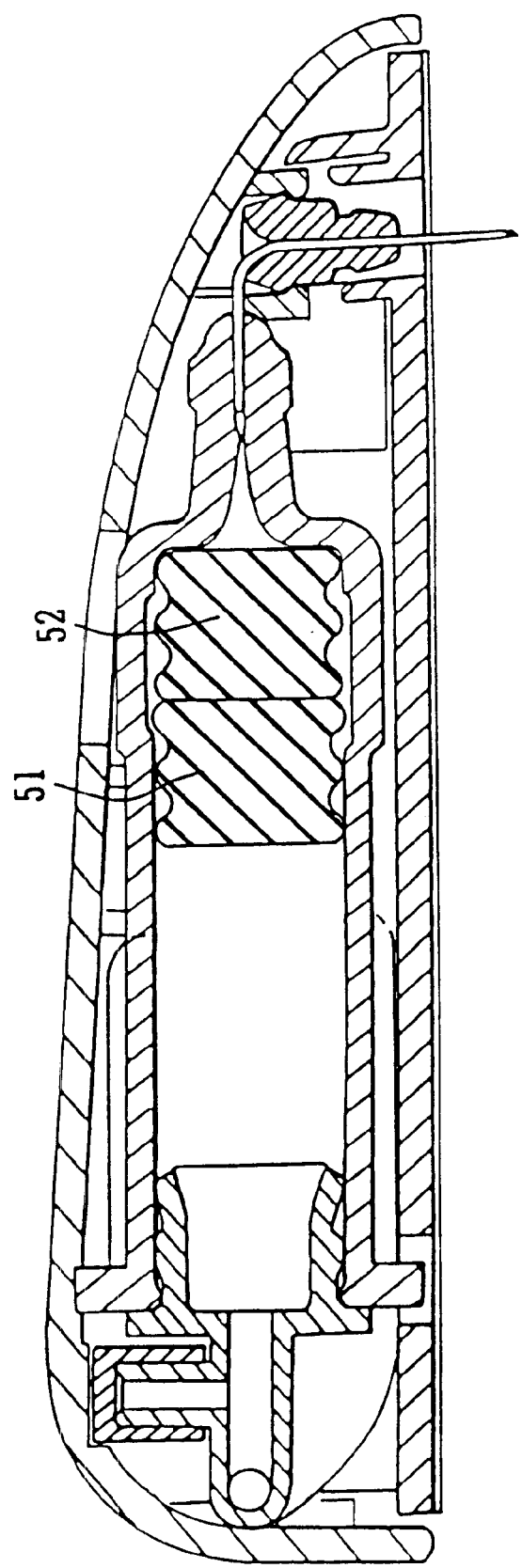

Although a certain amount of air is pushed through needle 17 ahead of the drug solution, the amount involved will not have any adverse effect if delivery is subcutaneous. The design of the device can also be optimised to minimise or eliminate air from being delivered. Delivery of drug continues until the position shown in FIG. 22 is reached, wherein end piston 51 and internal piston 52 have travelled the maximum distance and substantially all drug has been delivered.

It should be noted that the barrel 50 and pistons 51,52 are shaped such that gas cannot be pumped to the patient after delivery of the drug is completed.

Figure 23:
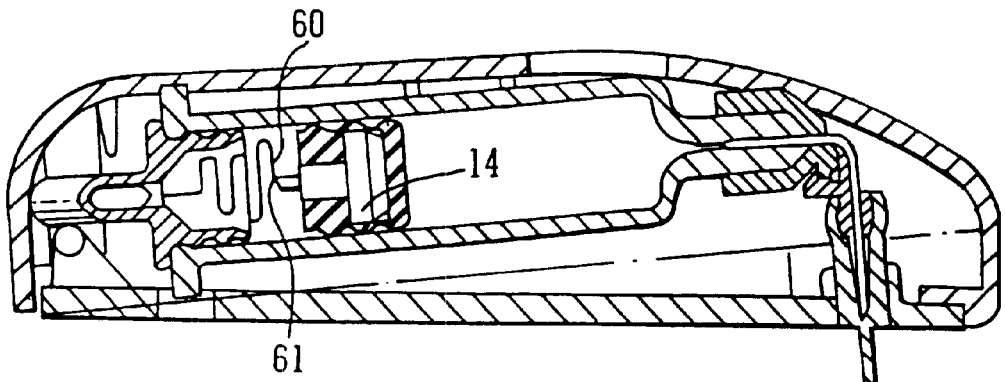
FIG. 23 is a sectional side view of a further variation on the device of FIG. 1.
Figure 24:
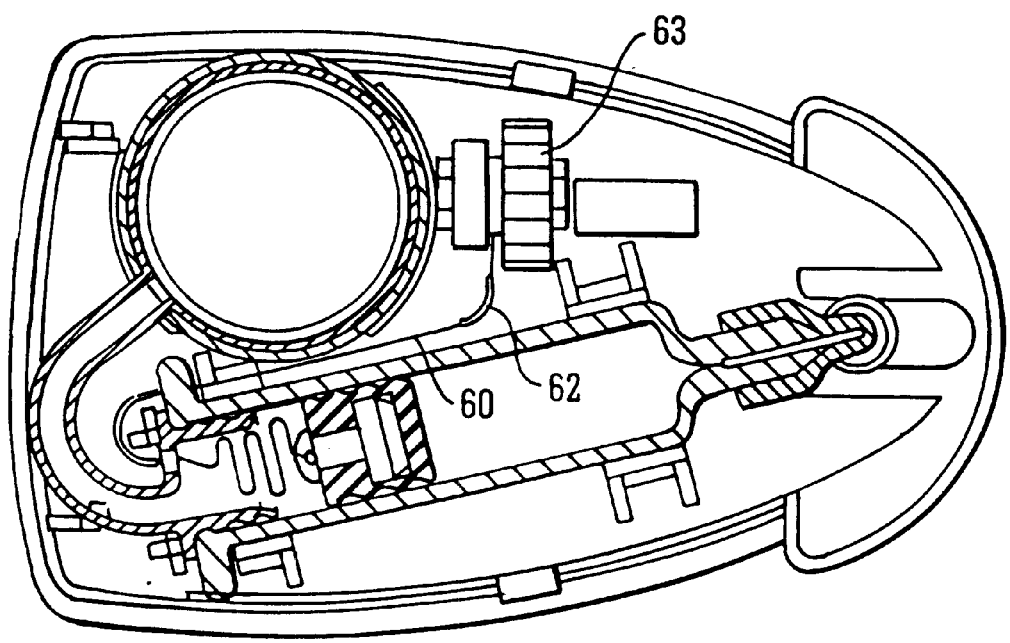
FIG. 24 is a sectional plan view of the device of FIG. 23.

FIG. 23 shows a further feature which may be incorporated into devices according to the invention. A travel limiting mechanism is provided to limit the maximum amount of travel of a piston 14 along the length of a syringe barrel 12. The travel limiting mechanism comprises an adjustable length of fish line 60 connected at one end 61 thereof to the piston 14 and at the other end 62 thereof (FIG. 24) to length adjustment means in the form of a knurled wheel 63 which can be rotated to shorten or lengthen the line 60. The line can provide from 100% travel down to 70% travel depending on the setting of the wheel 63. The wheel may be adjustable by the patient or it may be designed to prevent patient tampering and to allow only a physician or pharmacist to make adjustments.

The advantage of this arrangement is that it converts the device of FIG. 1 from a single dose device to one in which the dose can be adjusted to suit individual patients. Many drugs are administered on a "body weight basis" (e.g. a certain number of milligrams of drug per kilogram body weight), and so the dosage must be varied to suit each patient. By providing a series of devices with complementary dosages, a manufacturer may be able to cater for a broad selection of patients.

For example in a series of two devices (sizes "A" and "B"), each being adjustable to deliver from 70% to 100% of the total pre-filled dose, size "A" may contain 100 units (arbitrary units). Thus, device "A" can deliver from 70 to 100 units by adjustment of suitable travel limiting means. If device "B" is pre-filled with 70 units, then it can deliver from 70% to 100% of this dose, i.e. from 49 to 70 units. Thus, with only two devices, doses from 100 units down to less than 50 units can be catered for, covering a wide range of patients on a mg/kg dosage basis. Adding third or fourth device sizes to the series extends the possible delivery amounts even further.

It is to be understood that the illustrated travel limiting means are intended only for illustrative purposes and that a wide variety of equivalent means to control the dosage delivered may be employed.

Furthermore, while the invention has been shown with a simple gas generator which delivers the drug at a rate determined by the mixing of an effervescent couple, the gas generator could also be a more sophisticated, controllable generator, such as an electrolytic cell which generates gas at a rate determined by a current which is electronically controlled.

As used herein, the term, "drug", is meant to encompass any drug-containing fluid capable of being passed through a hollow needle in a controlled manner, such as a liquid, solution, gel or fine suspension. The term "drug" used herein includes but is not limited to peptides or proteins (and memetics thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides, proteins or hormones (or any memetic or analogues of any thereof) such as insulin, calcitonin, calcitonin gene regulating protein, atrial natriuretic protein, colony stimulating factor, betaseron, erythropoietin (EPO), interferons such as $\alpha$, $\beta$ or $\gamma$ interferon, somatropin, somatotropin, somastostatin, insulin-like growth factor (somatomedins), luteinizing hormone releasing hormone (LHRH), tissue plasminogen activator (TPA), growth hormone releasing hormone (GHRH, oxytocin, estradiol, growth hormones, leuprolide acetate, factor VIII, interleukins such as interleukin-2, and analogues or antagonists thereof, such as IL-1ra; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiazines, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluoxamine, Bisolperol, tactolimuls, sacrolimus and cyclosporin.

It will further be appreciated that many of the embodiments discussed above are preferred embodiments, falling within the scope of the invention, and that various alternative embodiments are contemplated.

What is claimed is:

1. A drug delivery device comprising:

a housing having an internal drug reservoir;

a drug delivery needle extending from the housing for penetration of the skin of a subject, the needle having an outlet for drug delivery;

a base member defining a skin-contacting surface for application to the skin of a subject, said base member being in pivotable relation to the housing between a first position in which the needle is concealed from the exterior of the device and a second position in which the delivery needle protrudes from the device for penetration of the skin, the device further comprising means for locking the device in the first position after a single reciprocation of the device from the first position to the second position and back to the first position.

2. A device according to claim 1, wherein a sealing sheath is provided with a flexible pull tab which extends through a release liner.

3. A device according to claim 2, wherein when the pull tab is pulled away from the base member, the release liner is pulled away from a lower surface of the base member and the sealing sheath is detached from a mounting member to reveal the needle tip.

4. A device according to claim 3, which is provided with a removable locking member which prevents relative movement of the base member towards the housing following removal of the sealing sheath and the release liner, thereby retaining the needle within the housing until skin penetration is required.

5. A device according to claim 4, wherein said removable locking member is a semi-rigid safety tab.

6. A device according to claim 4, wherein movement of the base member relative to the housing is initially prevented by said removable locking member.

7. A device according to claim 6, additionally comprising means for providing a gas for delivering a drug from the reservoir through the needle, and wherein the presence of said removable locking member also prevents the means for providing a gas from being actuated.

8. A device according to claim 6, wherein said removable locking member comprises a laminar member inserted between said base member and said housing.

9. A device according to claim 1, wherein the locking means comprises a mechanical latch which is brought into operation by said reciprocation.

10. A device according to claim 9, wherein said latch comprises a pair of elements mounted on the base member and the housing respectively, said elements being shaped such that they can have two relative configurations when the base member is in said first position relative to the housing, namely a movable configuration in which the elements are mutually movable, and a locked configuration in which the elements are prevented from mutual movement, and wherein reciprocation of the base member and the housing causes the elements to pass from the first movable configuration, through an intermediate configuration when the base member is in said second position relative to the housing, and then to said locked configuration, thereby preventing any further movement of the base member relative to the housing.

11. A device according to claim 10, wherein one of said elements is provided with a recess which is adapted to receive a projection on the other of said elements, the recess and the projection being spaced apart from one another in the movable configuration, and being in engagement with one another in the locked configuration.

12. A device according to claim 1, additionally comprising means for providing a gas for delivering a drug from the reservoir through the needle and a release valve, and wherein following delivery of the drug through the needle, any residual gas is vented through said release valve.

13. A device according to claim 1, wherein the locking means comprises a mechanical latch which is brought into operation by said reciprocation.

14. A device according to claim 13, wherein said latch comprises a pair of elements mounted on the base member and the housing respectively, said elements being shaped such that they can have two relative configurations when the base member is in said first position relative to the housing, namely a movable configuration in which the elements are mutually movable, and a locked configuration in which the elements are prevented from mutual movement, and wherein reciprocation of the base member and the housing causes the elements to pass from the first movable configuration, through an intermediate configuration when the base member is in said second position relative to the housing, and then to said locked configuration, thereby preventing any further movement of the base member relative to the housing.

15. A device according to claim 14, wherein one of said elements is provided with a recess which is adapted to receive a projection on the other of said elements, the recess and the projection being spaced apart from one another in the movable configuration, and being in engagement with one another in the locked configuration.

16. A device according to claim 1, wherein movement of the base member relative to the housing is initially prevented by a removable locking member.

* * * * *